(12) United States Patent
Yang et al.

(10) Patent No.: US 11,364,312 B2
(45) Date of Patent: Jun. 21, 2022

(54) PLATINUM SULFIDE PROTEIN NANOPARTICLE HAVING NEAR-INFRARED PHOTOTHERMAL EFFECT AND MULTIMODAL IMAGING FUNCTION, PREPARATION METHOD THEREFOR AND APPLICATION THEREOF

(71) Applicant: SOOCHOW UNIVERSITY, Suzhou (CN)

(72) Inventors: Hong Yang, Suzhou (CN); Huabing Chen, Suzhou (CN); Xue Wang, Suzhou (CN); Hengte Ke, Suzhou (CN); Ming Li, Suzhou (CN); Tao Xu, Suzhou (CN); Miya Zhang, Suzhou (CN)

(73) Assignee: SOOCHOW UNIVERSITY, Suzhou (CN)

(*) Notice: Subject to any disclaimer, the term of this patent is extended or adjusted under 35 U.S.C. 154(b) by 0 days.

(21) Appl. No.: 17/169,455

(22) Filed: Feb. 6, 2021

(65) Prior Publication Data
US 2021/0154336 A1   May 27, 2021

Related U.S. Application Data

(63) Continuation of application No. PCT/CN2018/099268, filed on Aug. 7, 2018.

(51) Int. Cl.
| | |
|---|---|
| *A61K 49/22* | (2006.01) |
| *A61K 9/51* | (2006.01) |
| *A61K 41/00* | (2020.01) |
| *A61K 49/00* | (2006.01) |
| *A61K 49/04* | (2006.01) |

(52) U.S. Cl.
CPC .......... *A61K 49/225* (2013.01); *A61K 9/5115* (2013.01); *A61K 9/5169* (2013.01); *A61K 9/5192* (2013.01); *A61K 41/0052* (2013.01); *A61K 49/0002* (2013.01); *A61K 49/0056* (2013.01); *A61K 49/04* (2013.01)

(58) Field of Classification Search
CPC .. A61K 49/0002; A61K 49/04; A61K 49/225; A61K 49/0056; A61K 9/5169; A61K 9/5192; A61K 9/5115; A61K 41/0052; C07K 1/107; A61P 35/00
See application file for complete search history.

(56) References Cited

FOREIGN PATENT DOCUMENTS

| CN | 101074093 A | * | 11/2007 | ............. C01B 17/20 |
|---|---|---|---|---|
| CN | 104587493 A | | 5/2015 | |
| CN | 105056233 A | | 11/2015 | |
| CN | 105106958 A | | 12/2015 | |
| CN | 106267198 A | | 1/2017 | |
| CN | 107551279 A | | 1/2018 | |

OTHER PUBLICATIONS

Tang et al., "Albumin-coordinated assembly of clearable platinum nanodots for photo-induced cancer theranostics" Biomaterials 154 (2018) 248-260 (Oct. 20, 2017).

* cited by examiner

*Primary Examiner* — Michael G. Hartley
*Assistant Examiner* — Leah H Schlientz
(74) *Attorney, Agent, or Firm* — SZDC Law P.C.

(57) ABSTRACT

A platinum sulfide protein nanoparticle having near-infrared photothermal effect and multi-modal imaging function, a preparation method therefor and an application thereof. The platinum sulfide nanoparticle having near-infrared photothermal effect and multi-modal imaging function is prepared in aqueous phase by means of formulation screening and process limitation. The nanoparticle has an ultra-small particle size and good stability as well as tumor targeting and photothermal effects and integrates functions of near-infrared imaging, CT imaging, and thermal imaging, so as to achieve high sensitivity, high resolution, and precise positioning of tumors, and to produce high-efficiency photothermal effects under the excitation of near-infrared light to kill tumor cells by thermal ablation, thereby achieving the purpose of efficient, safe, visual, and accurate treatment of tumors. The nanoparticle has the potential for further development and clinical application.

4 Claims, 9 Drawing Sheets

PLATINUM SULFIDE PROTEIN NANOPARTICLE HAVING NEAR-INFRARED PHOTOTHERMAL EFFECT AND MULTIMODAL IMAGING FUNCTION, PREPARATION METHOD THEREFOR AND APPLICATION THEREOF This application is a Continuation Application of PCT/CN2018/099268, filed on Aug. 7, 2018, which is incorporated by reference for all purposes as if fully set forth herein.

TECHNICAL FIELD

The invention discloses a preparation method and application thereof of an ultra-small platinum sulfide protein nanoparticle having near-infrared photothermal effect and multi-modal imaging function.

BACKGROUND TECHNIQUE

Malignant tumors are one of the major malignant diseases that seriously threaten human health, and their morbidity and mortality have increased significantly at home and abroad. How to achieve accurate diagnosis and efficient treatment of tumors is the focus and difficulty of current research. Since temperature is an important parameter that affects enzyme activity and various biochemical reaction rates in the body, an increase in body temperature usually means infection or other diseases. Through external near-infrared light irradiation, the nanomaterials containing photothermal reagents that enter tumor cells can absorb light and convert it into heat, which can lead to apoptosis or even ablation, which has become the current method of photothermal treatment of tumors. Compared with surgical resection, radiation therapy, and chemotherapy, the advantages of photothermal therapy are non-invasive, targeted, efficient, and non-invasive. The near-infrared light applied by it is different from ultraviolet light or visible light, and can penetrate into the tissue to a certain extent without causing abnormality and damage to the tissue at a relatively low intensity. As the main body of heat production, photothermal reagents play a key role in photothermal therapy. Its performance has a decisive influence on the effect of photothermal therapy, and accurate diagnosis is a prerequisite for effective treatment.

Due to various shortcomings of traditional photothermal agents, the effect of photothermal treatment is severely restricted. Nanomaterials play a vital role in improving the performance of photothermal agents. "Platinum element" is a precious metal element, which is located next to "gold element" in the periodic table. Compared with gold, platinum drugs have been more successful in the field of tumor treatment. In addition to traditional platinum drugs, nanoparticles of platinum compounds also have potential anticancer activity and certain photothermal effects. However, there are still some obvious defects in currently reported platinum nanoparticles, including: (1) platinum nanoparticle light Poor thermal effect, slow heating, and need to enhance the killing effect on cells; (2) In the process of synthesizing platinum nanoparticles, in order to control the growth of platinum particles or form stable platinum nanoparticles, some are not accepted by clinical injection Components (such as PVP or dendrimers), which will inevitably increase the toxicity of the product and reduce the possibility of clinical transformation. (3) The existing platinum nanoparticles do not have imaging capabilities and cannot provide a diagnosis and treatment solution for tumor treatment. Therefore, it is necessary to further explore the potential of platinum nanoparticles in the diagnosis and treatment of tumors, and adopt more scientific and effective preparation methods to obtain high-performance platinum nano reagents for clinical use that are safer and have both diagnostic and therapeutic functions for tumors. Photo-Thermal Therapy (PTT).

CT contrast agents currently in clinical use, such as iopromide, are likely to cause tumor targeting imaging and angiography failure due to pharmacokinetic limitations such as short half-life in the circulation and non-specific distribution. In addition, CT imaging has some inherent limitations, especially because of the poor contrast between tumor tissue and soft tissue, which is not easy to distinguish, and has shortcomings such as radiation, which is the shortcoming of CT in clinical diagnosis.

Protein nanocarriers have attracted much attention due to their good biocompatibility. In addition to the protein molecules currently reported, albumin can be used as a protein nanoreactor, and the sulfhydryl group contained in the protein can be used as the source of sulfur element to prepare nanosulfide nanoparticle, or use the protein reactor for encapsulation. Two compounds, bismuth sulfide and thorium oxide, are used in the diagnosis and treatment of tumors.

However, there have been no reports of platinum sulfide used for photothermal therapy, and the prior art has not seen any nano-agents containing a platinum-based compound that can simultaneously perform photothermal and four-mode modern imaging diagnosis. effect

Technical Problem

In order to solve the above technical problems, an object of the present invention is to provide a platinum sulfide protein nanoparticle having near-infrared photothermal effect and multi-modal imaging function and a preparation method thereof, which has good biological safety, tumor targeting and retention At the same time, it has the ability to accurately identify tumors by near-infrared fluorescence imaging, photoacoustic imaging, CT imaging, and thermal imaging, and can generate efficient photothermal effects under the excitation of near-infrared light to kill tumor cells, achieving efficient, safe, and precise treatment of tumors. Preparation and Application of Multifunctional Albumin Nanoparticles.

Because different imaging technologies have their own advantages and disadvantages, the combined application of the four modal imaging can better complement each other: near-infrared fluorescence (NIRF) imaging has high sensitivity and strong contrast; photoacoustic (PA) imaging can present microstructures and distinguish High rate; X-ray computed tomography (CT) imaging has good penetrability and accurate three-dimensional spatial positioning; thermal ($\Delta T$) imaging can grasp the scope of the tumor by heating up the area. Their combined advantages complement each other to provide more accurate positioning for subsequent PTT, and to more effectively monitor and evaluate the treatment effect.

Technical Solutions

The present invention adopted technical scheme as follow: a platinum sulfide protein nanoparticle with near-infrared photothermal effect and multi-modal imaging function, the nanoparticle is prepared in the water 0-55° C., for 0 to 5 h, a particle size of 1 to 5 nm. Generally, the nanoparticles with different particle sizes have different behaviors in different organs due to the biofilm effect. Ultra-small nanoparticles with the particle size smaller than 5 nm can be eliminated from the body by the kidney. Therefore, the ultra-small inorganic nanoparticles prepared with the mild conditions of the present invention. Not only provided a more secure platform for multimodal imaging and tumor treatment, but also it was particularly prominent for the significance of the inorganic nanoparticles that were difficult to degrade in the body.

In the above technical solution, the protein is albumin and serves as the scaffold of the nanoparticle. In the preparation reaction, the platinum source is platinum dichloride; and the sulfur source is sodium sulfide.

The invention also disclosed a method of preparing platinum sulfide protein nanoparticle with near-infrared photothermal effect and multi-modal imaging function, which includes the following steps: mixing a platinum dichloride solution with a protein solution, and adding a sodium sulphide solution to the mixture; and the mixture is then dialyzed and ultrafiltrated, to obtain the platinum sulfide protein nanoparticle with near-infrared photothermal effect and multi-modal imaging function.

The invention also disclosed a method of preparing a reagent with near-infrared photothermal effect and multi-modal imaging function that includes the following steps: mixing a platinum dichloride solution with a protein solution, and adding a sodium sulphide solution to the mixture; and the mixture is then dialyzed and ultrafiltrated to obtain the platinum sulfide protein nanoparticle with near-infrared photothermal effect and multi-modal imaging function; dispersing the nanoparticle with deionized water to obtain the reagent with near-infrared photothermal effect and multi-modal imaging function.

In the invention, the concentration of the platinum dichloride solution is 2 to 8 mmol/L; the concentration of the protein solution is 1 to 9 mg/mL; and the concentration of the sodium sulphide solution is 1-50 mmol/L; the volume ratio of the platinum dichloride solution, the protein solution, and the sodium sulfide solution is 1:0.2:0.05; and the dispersion agent is water.

In the invention, the reaction temperature is 0 to 55° C., the reaction time is for 0 to 5 h. the cut-off molecular weight for dialyzing is 3500 kD, the dialysis time is 1 to 24 hours, the receiving medium is deionized water, and the receiving medium is changed 6 to 8 times, the cut-off molecular weight for ultrafiltration centrifugation is 100 kD, the rotation speed of the ultrafiltration centrifugation is 1500 to 4000 r/min, and the number of ultrafiltration centrifugation is at least 20 times.

The invention discloses the platinum sulfide protein nanoparticle with near-infrared photothermal effect and multi-modal imaging function or the reagent with near-infrared photothermal effect and multi-modal imaging function according to the methods described herein. The diameter of platinum sulfide protein nanoparticle with near-infrared photothermal effect and multi-modal imaging function is 1 to 5 nm. The protein was the scaffold of the nanoparticle and the platinum sulfide is the core of the nanoparticle.

The invention discloses that the platinum sulfide protein nanoparticle with near-infrared photothermal effect and multi-modal imaging function or the reagent with near-infrared photothermal effect and multi-modal imaging function is applied in the nano preparations integrated for cancer diagnosis and treatments with near-infrared photothermal effect and multi-modal imaging function. The multi-modality imaging includes near-infrared fluorescence imaging, photoacoustic imaging, X-ray computed tomography imaging, and thermal imaging.

The invention discloses a method of preparing a platinum sulfide protein nanoparticle with near-infrared photothermal effect and multi-modal imaging function that includes the following steps:

(1) Mixing a platinum dichloride solution and a protein solution to obtain a mixed solution, the platinum dichloride concentration is 2 to 8 mmol·L$^{-1}$, and the concentration of the protein solution concentration is 1 to 9 mg·mL$^{-1}$;

(2) Adding sodium sulfide solution to the mixed solution of step (1), the concentration of the sodium sulfide solution is 1 to 50 mmol·L$^{-1}$, and then reacting the mixed solution at 0 to 55° C. for 0 to 5 hours;

(3) Placing the mixture solution of step (2) in a dialysis bag (with a cut-off molecular weight of 3500) for dialysis for 1 to 24 hours to remove unreacted reaction materials to obtain dialyzed nanoparticles, and then ultrafiltration purification is performed on the dialyzed nanoparticles (ultrafiltration tube cut-off molecular weight is 100 kD) to obtain the platinum sulfide protein nanoparticle with near-infrared photothermal effect and multi-modal imaging function.

In the present invention, deionized water is the receiving medium in the dialysis. The dialysis receiving medium is replaced 6 to 8 times; the rotation speed of the ultrafiltration centrifuge is 1500-4000 r·min$^{-1}$, and the number of the ultrafiltration centrifuge is at least 20 times.

The nanoparticles of the present invention have the following advantages: 1) strong X-ray attenuation ability, long in vivo circulation time, low toxicity, no residue, convenient preparation, low cost, small dosage and flexible use, etc., and can be used as an effective clinical CT contrast agent; 2) higher near-infrared absorption coefficient, based on near-infrared photoacoustic effect and heating effect, and 3) subsequent thermal expansion photoacoustic imaging function, which can provide higher spatial resolution distinguishing from soft tissue and used for real-time monitoring. Therefore, nanoparticles are very promising in photothermal therapy and near-infrared imaging, photoacoustic imaging, CT imaging, and thermal imaging applications.

The invention disclosed the platinum sulfide protein nanoparticle with near-infrared photothermal effect and multi-modal imaging function or the reagent with near-infrared photothermal effect and multi-modal imaging function, there is two parts, the core is platinum sulfide, and the scaffold is albumin. Protein as a nanoreactor can produce a variety of protein nanoparticles with different functions, which can form nanocomplexes with metal ions through electrostatic adsorption or special site binding. A precipitation reaction occurs in the swollen protein cavity and induces inorganic nanometers. Crystals nucleate and grow, showing good biocompatibility and tumor targeting, enabling early diagnosis and efficient treatment of tumors. The platinum sulfide protein nanoparticles of the present invention are protein nanoparticles prepared under mild conditions: the size is extremely small (1 to 5 nm), and the drug load is high (15.6%). The current drug load of existing nanoparticles is generally less than 10%, Has good photothermal effect, and shows great application prospect in targeted multimodal imaging guided cancer treatment.

Beneficial Effects

The platinum sulfide protein nanoparticles with near-infrared photothermal effect and multi-modal imaging function obtained by the present invention are used as near-infrared photothermal treatment preparations for tumors, near-infrared fluorescent imaging probes, photoacoustic imaging probes, CT imaging contrast agents, and thermal imaging agents. Imaging probe applications have the following advantages:

(1) The present invention uses albumin as a nanoreactor to prepare ultra-small-sized protein nanoparticles under mild conditions. The reaction method is simple, the conditions are mild, and the time is short (reaction 0 to 5 h at 0 to 55° C.), compared with existing proteins. Nanoparticles (complex system, high cost, long time) are more convenient to prepare, the sample is well dispersed, and the size range can be excreted by the kidney to the outside, which is more effective and safe;

(2) The nanoparticle of the present invention has high light-to-heat conversion efficiency (32.0%), high molar extinction coefficient ($1.11\times10^9$ $M^{-1} \cdot cm^{-1}$), and good light-heat stability (continuous light exposure for 15 min, no absorption spectrum and heating effect) (Significant attenuation); the light-to-heat conversion efficiency of the nanoparticles of the present invention is 32.0%, which is higher than that of gold nanorods (13%) and gold nanoparticle shells (21%), and is similar to palladium nanoplates (27.6%). Outstanding performance in nano reagents;

(3) The nanoparticle of the present invention has good tumor targeting, can be effectively taken up by tumor cells, has good biocompatibility, and is basically non-toxic in the dark field; and can be specified in the body after being precisely irradiated and excited by controllable near-infrared light in vitro. A strong thermal effect is generated on the part, which effectively eliminates tumors. It has near-infrared photothermal effect and near-infrared fluorescence, photoacoustic and X-ray computed tomography imaging, and multi-modal imaging functions of thermal imaging. It is a safe and effective nanometer preparation for integrated diagnosis and treatment.

BRIEF DESCRIPTION OF THE DRAWINGS

The platinum sulfide protein nanoparticle with near-infrared photothermal effect and multi-modal imaging function of the invention was referred to as "nanoparticles" for short.

Figure 3:
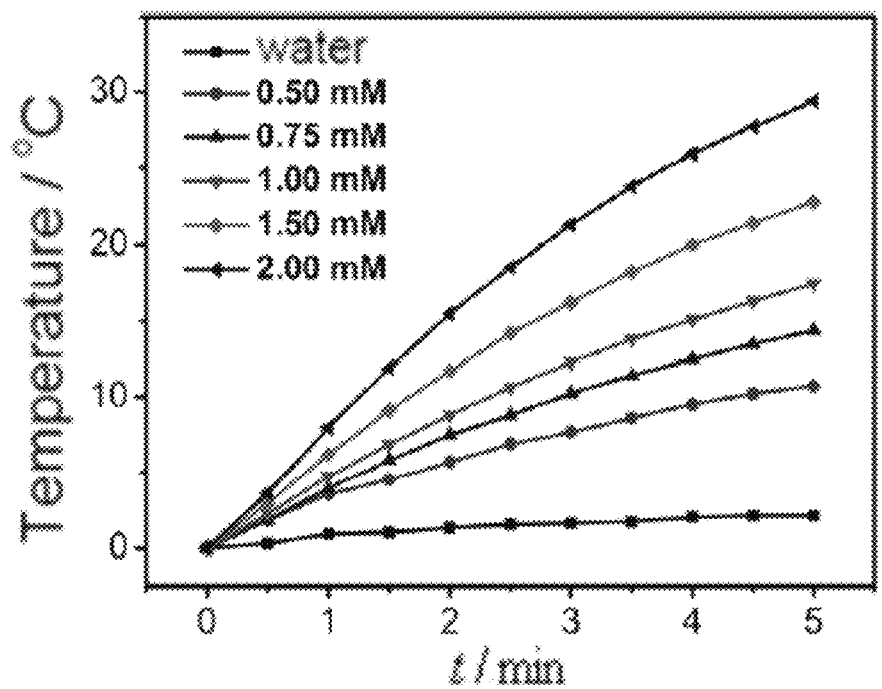
Figure 4:
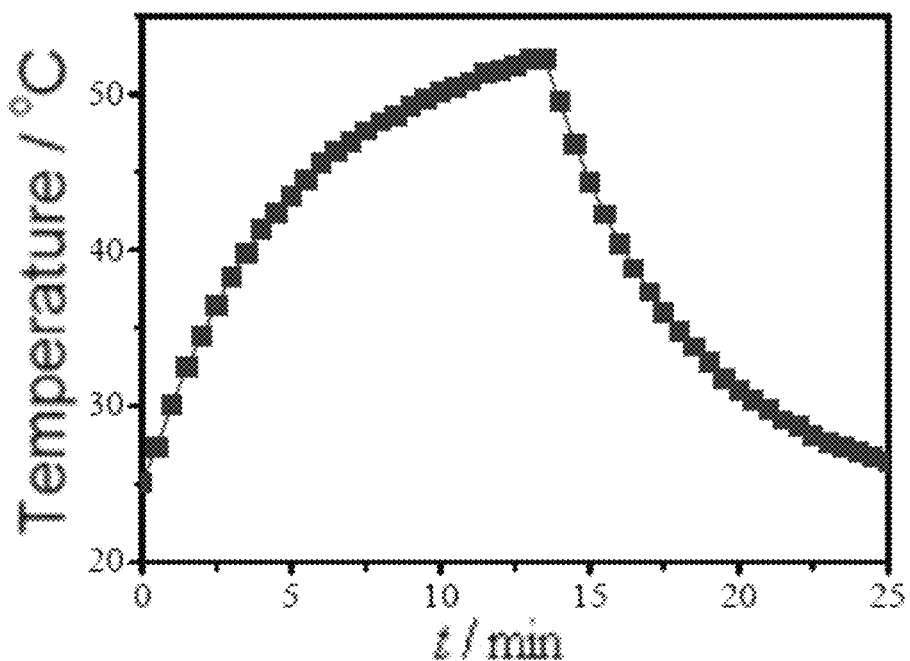
Figure 5:
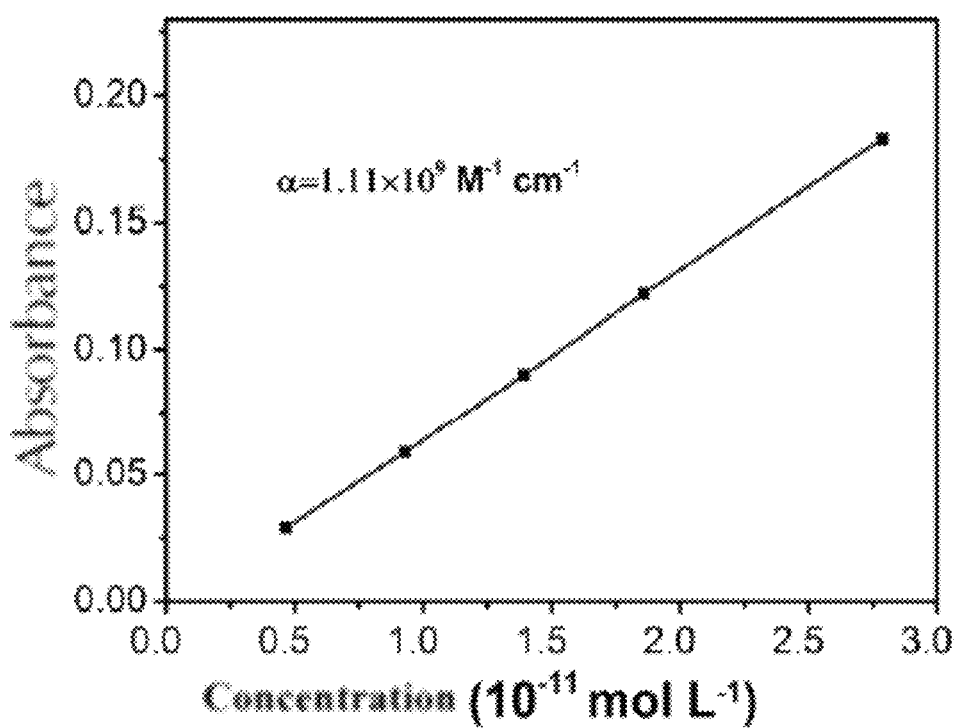
Figure 6:
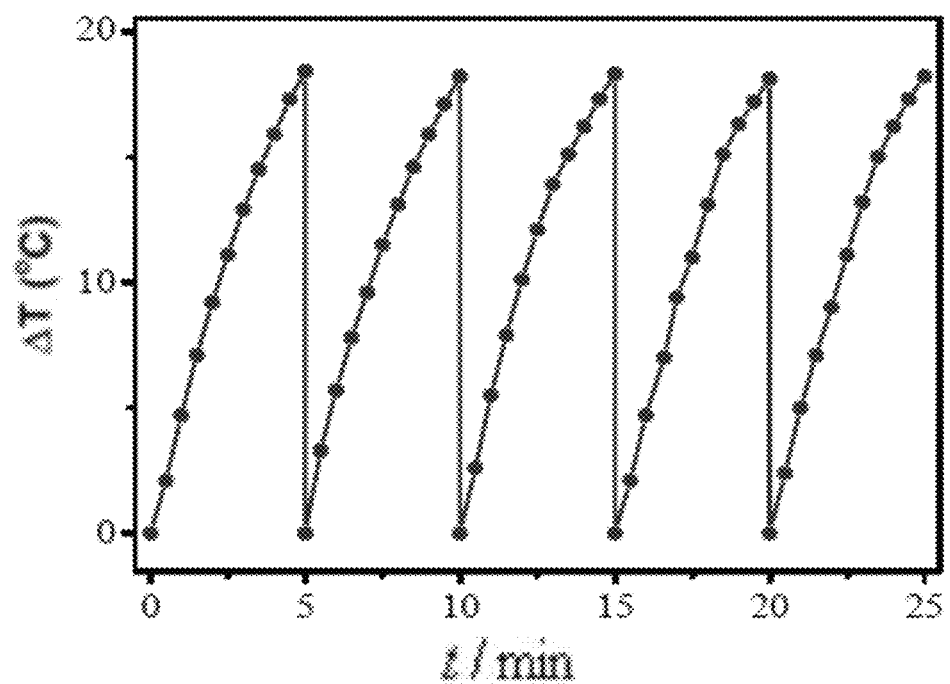
Figure 7:
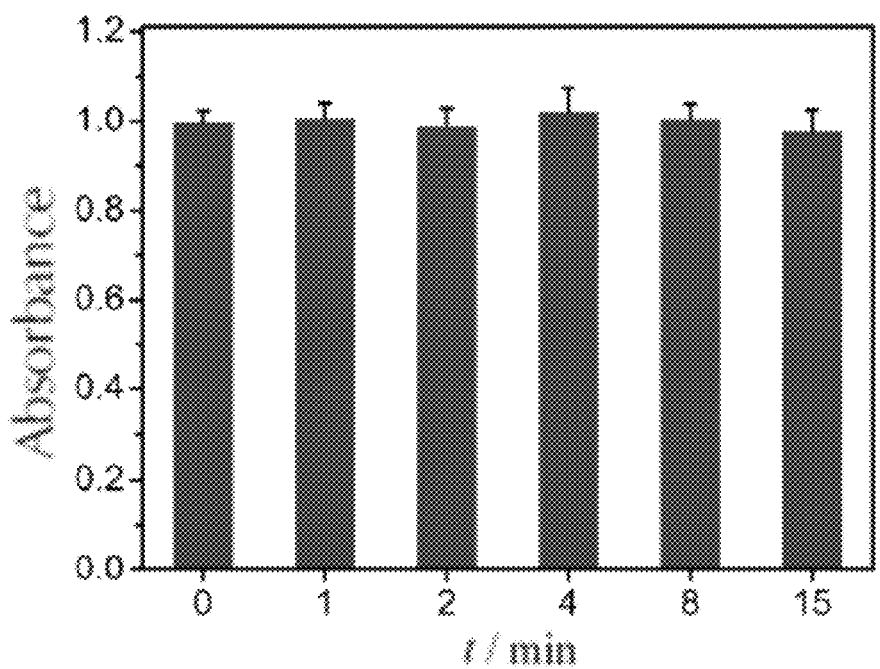
Figure 8:
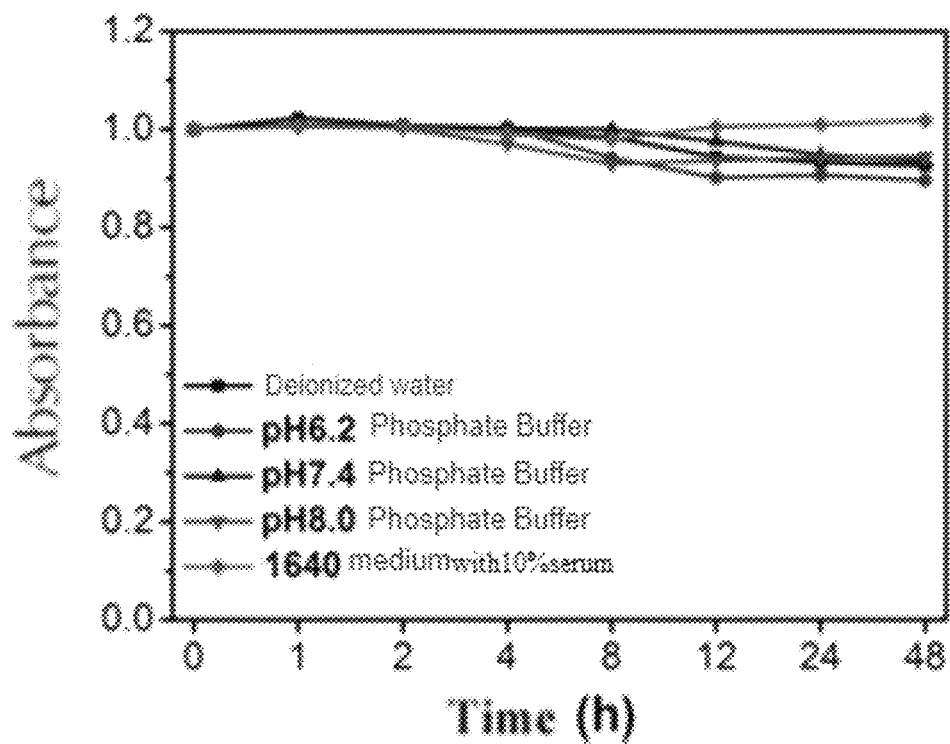
Figure 9:
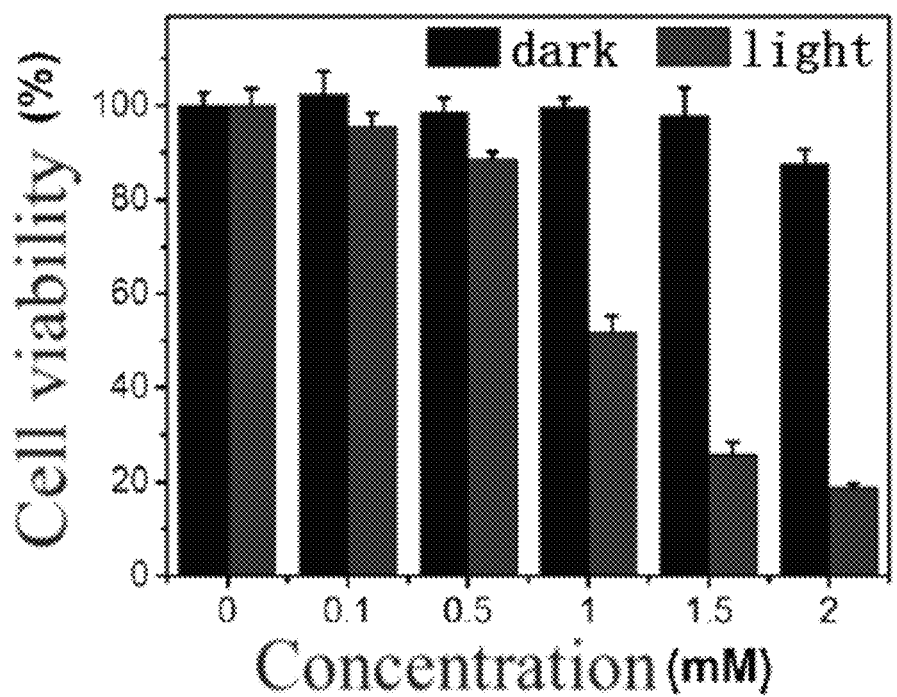
Figure 10:
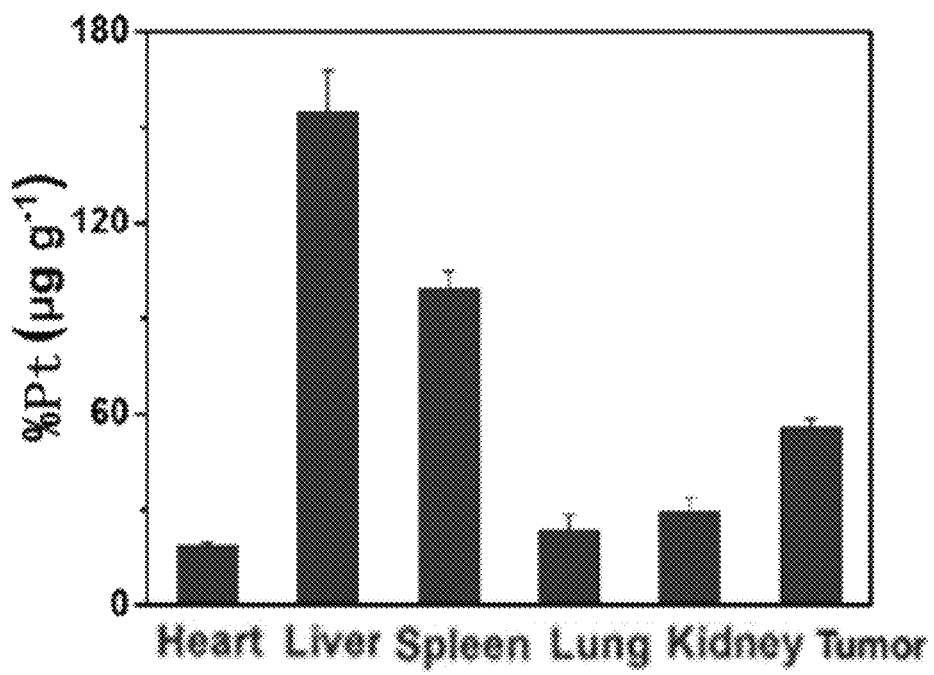
Figure 11:
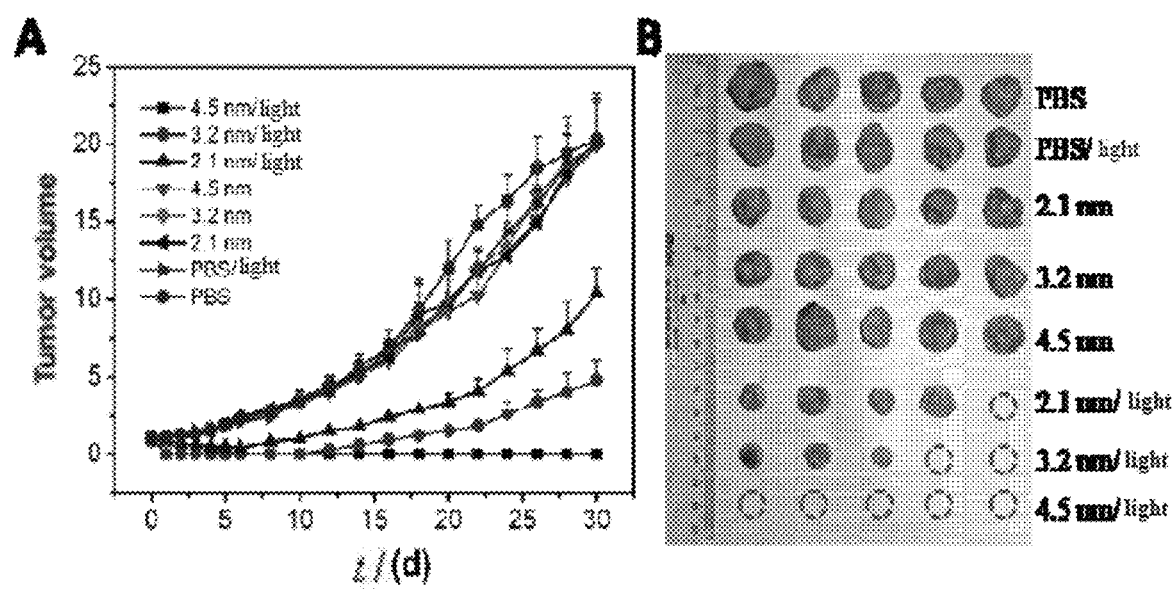
Figure 12:
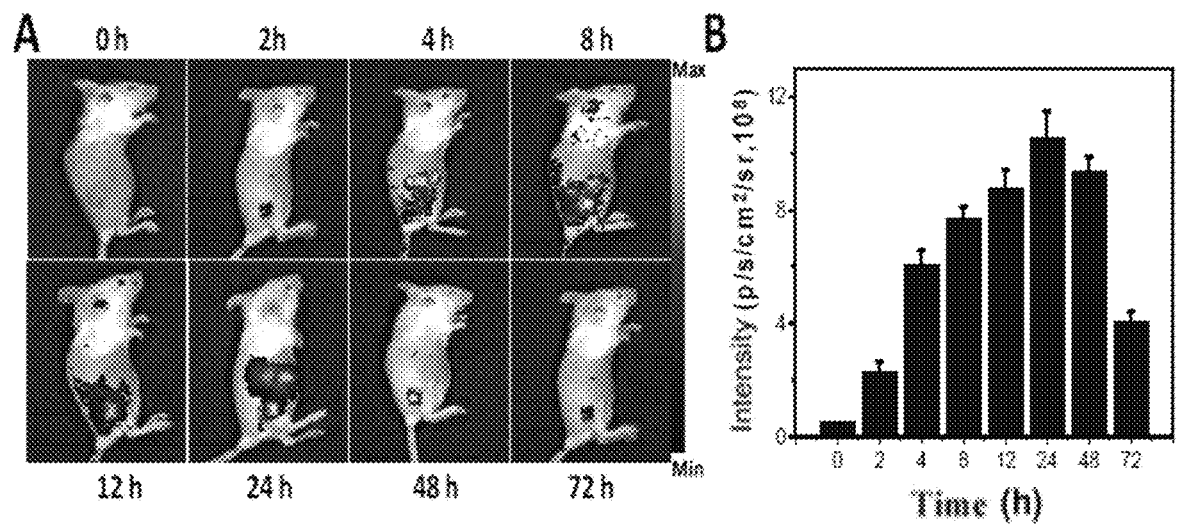
Figure 13:
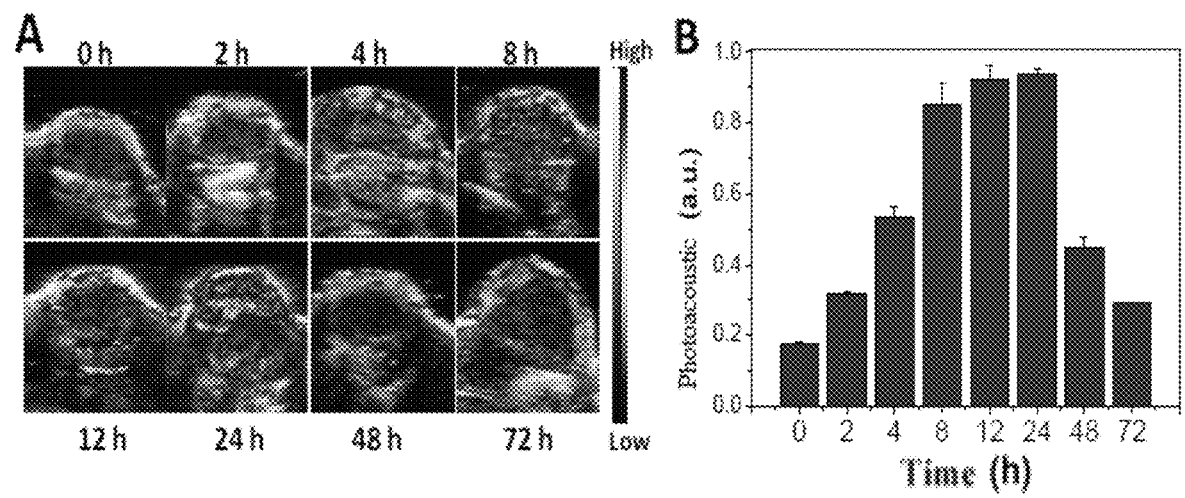
Figure 14:
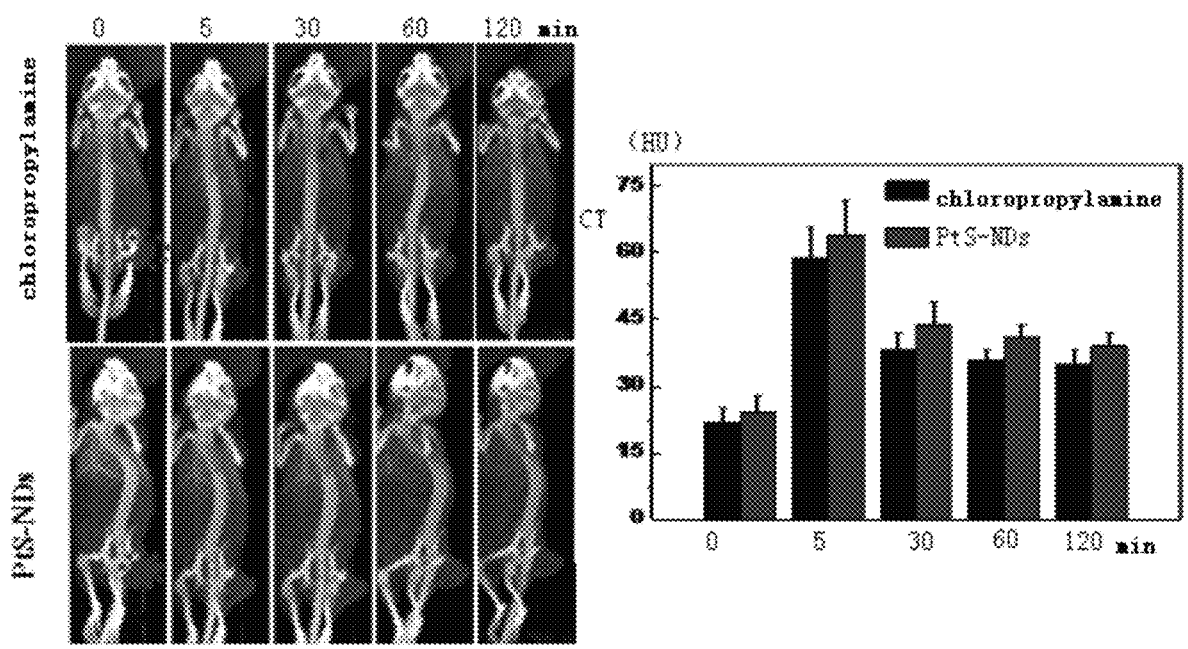
Figure 15:
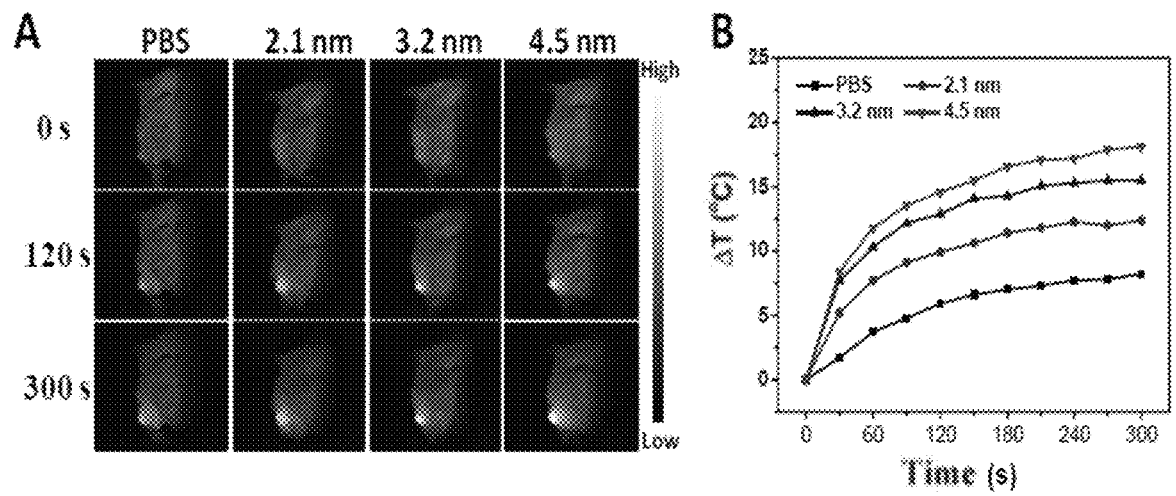
Figure 16:
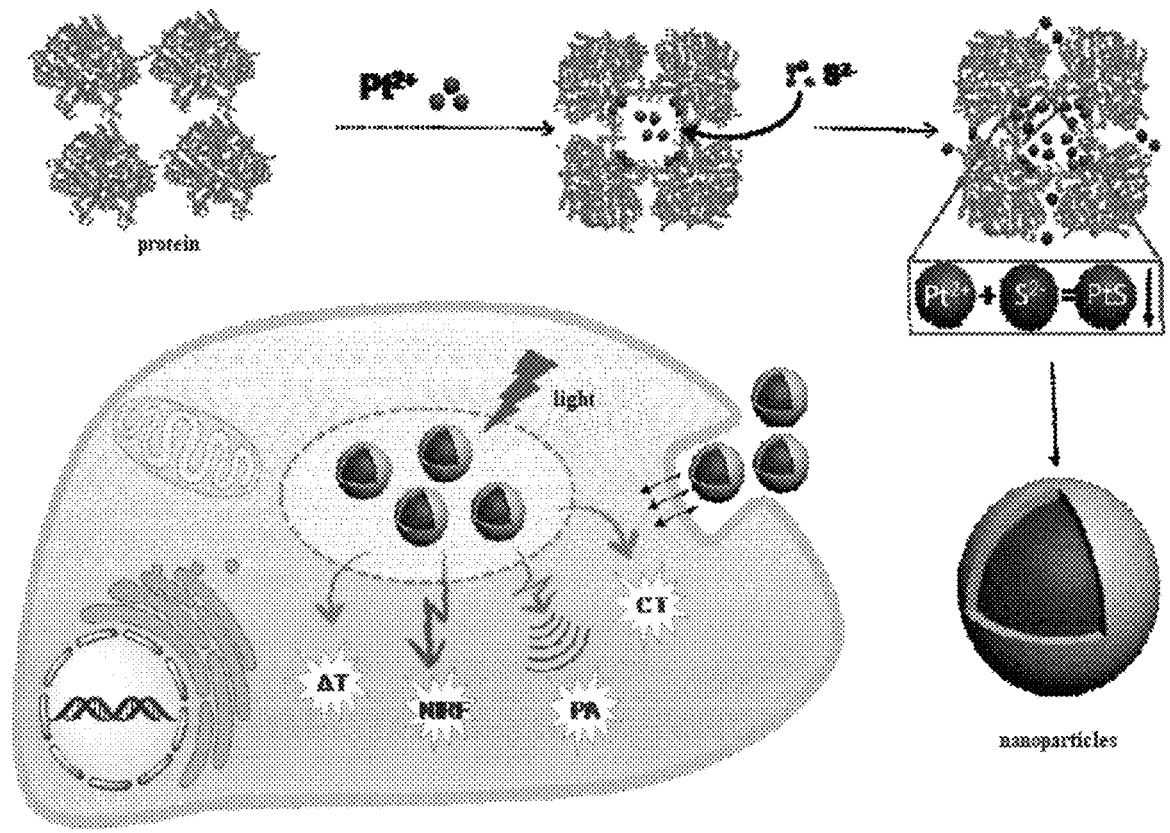

2A. hydrated particle size;

2B. Near-infrared spectrum measured by ultraviolet-visible spectrophotometer;

2C. Circular Dichroism, CD;

2D. X-ray photoelectron spectroscopy, XPS;

2E. Field emission transmission electron microscope (Tecnai G 2F20 S-TWIN, FEI) mapping;

FIG. 3 is the near-infrared heating curves of nanoparticles with different concentrations;

FIG. 4 is a graph of investigation results of light-to-heat conversion efficiency of nanoparticles;

FIG. 5 is a graph of investigation results of molar extinction coefficients of nanoparticles;

FIG. 6 is a graph shown the effect of the irradiation time of nanoparticles on heating and morphology;

FIG. 7 is a diagram of the results of examining the photostability of the nanoparticles;

FIG. 8 is a graph showing the results of investigations on the physical and chemical stability of the nanoparticles;

FIG. 9 is a graph showing the results of cytotoxicity investigation of nanoparticles on 4T1 cells;

FIG. 10 is a diagram showing the results of examining the distribution of nanoparticles;

FIG. 11 is a graph of experimental results of tumor suppression of the tumor-bearing mice by nanoparticles;

FIG. 12 is the near-infrared fluorescence image of nanoparticles;

FIG. 13 is the photoacoustic imaging diagram of nanoparticles;

FIG. 14 is the X-ray computed tomography image of nanoparticles;

FIG. 15 is the thermal imaging diagram of nanoparticles;

FIG. 16 shows the preparation and working mechanism of nanoparticles.

EMBODIMENTS OF THE INVENTION

The specific embodiments of the present invention are described in further detail below with reference to the drawings and embodiments. The embodiments are used to illustrate that the multi-modality imaging in the present invention includes near-infrared fluorescence imaging, photoacoustic imaging, X-ray computed tomography imaging, and thermal imaging, but is not limited thereto. The ultra-small platinum sulfide protein nanoparticles with near-infrared photothermal effect and multi-modal imaging function are referred to as "nanoparticles" for short.

Example 1 Preparation and Application of Nanoparticles

1. Preparation of nanoparticles: Weigh 20.0 mg of human serum albumin (HAS, molecular weight 66 KD) in 10.0 mL of deionized water, weigh 2.7 mg of platinum dichloride ($PtCl_2$, molecular weight was 265.99) and dissolve in 2 mL of deionized water. In medium, 9.6 mg of sodium sulfide ($Na_2S.9H_2O$, molecular weight: 240.18) was weighed and dissolved in 0.5 mL of deionized water. An aqueous platinum dichloride solution was slowly added to the protein solution and the two were thoroughly mixed, and then an aqueous sodium sulfide solution was added to the solution. The molar ratio of Pt:S in the solution was 1:4, and the volume ratio of the protein solution, platinum dichloride solution, and sodium sulfide solution was 1:0.2:0.05. The solution was placed in water bath at 55° C. and stirred vigorously for 4 h. After the reaction was completed, the reaction product was placed in a dialysis bag (cut-off molecular weight: 3500), and the unreacted reaction raw materials were removed by dialysis for 24 h with ultrapure water, and the dialysis medium was replaced by 7 times, followed by centrifugation at 2000 r/min for 5 minutes with ultrafiltration ion energy tube, and centrifugation after washing by 20 times ultrafiltration water to obtain a purified product: platinum sulfide protein nanoparticles with near-infrared photothermal effect and multi-modal imaging function, referred to as Nanoparticles (PtS-NDs).

In addition, the photosensitizer Cy 7.5 was protected without light, dissolved in a dimethyl sulfoxide solution, added to the prepared PtS-NDs aqueous solution, and stirred for 4 to 8 hours in the dark to obtain Cy 7.5-labeled PtS-NDs (Cy nanometers) for fluorescent tracing.

2. Investigation on the drug loading of nanoparticles: freeze-dry the prepared nanoparticles, weigh a certain amount of lyophilized powder, reconstitute it with an aqueous solution, and measure the Pt content in the solution by ICP. The drug loading (LE) was calculated by the following formula as 15.6%.

LE (%)=$W_e$÷$W_m$×100% (wherein We is content of Pt, Wm is mass of nanoparticles)

Figure 1:
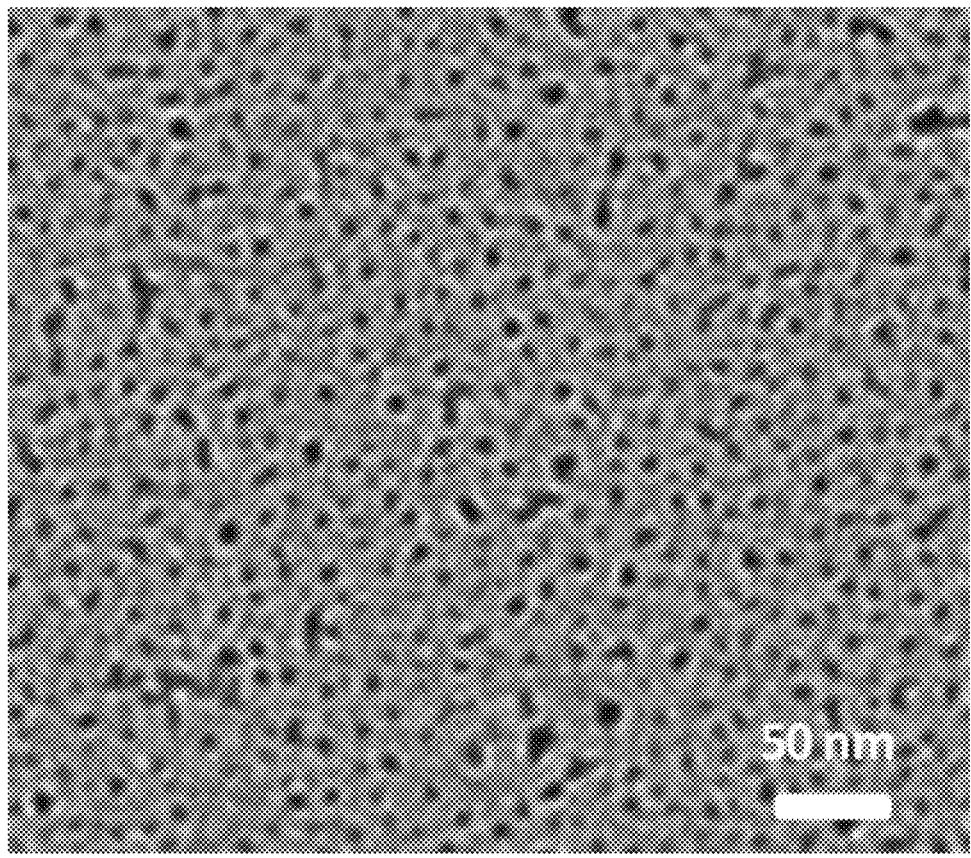
FIG. 1 is the transmission electron microscope characterization diagram of the nanoparticles.

3. TEM characterization of nanoparticles:

The transmission electron microscope image of the above nanoparticles shows that the prepared nanoparticles are a kind of uniformly dispersed ultra-small particle diameter nanoparticles with an average particle diameter of 4.5±0.4 nm, as shown in FIG. 1.

Figure 2:
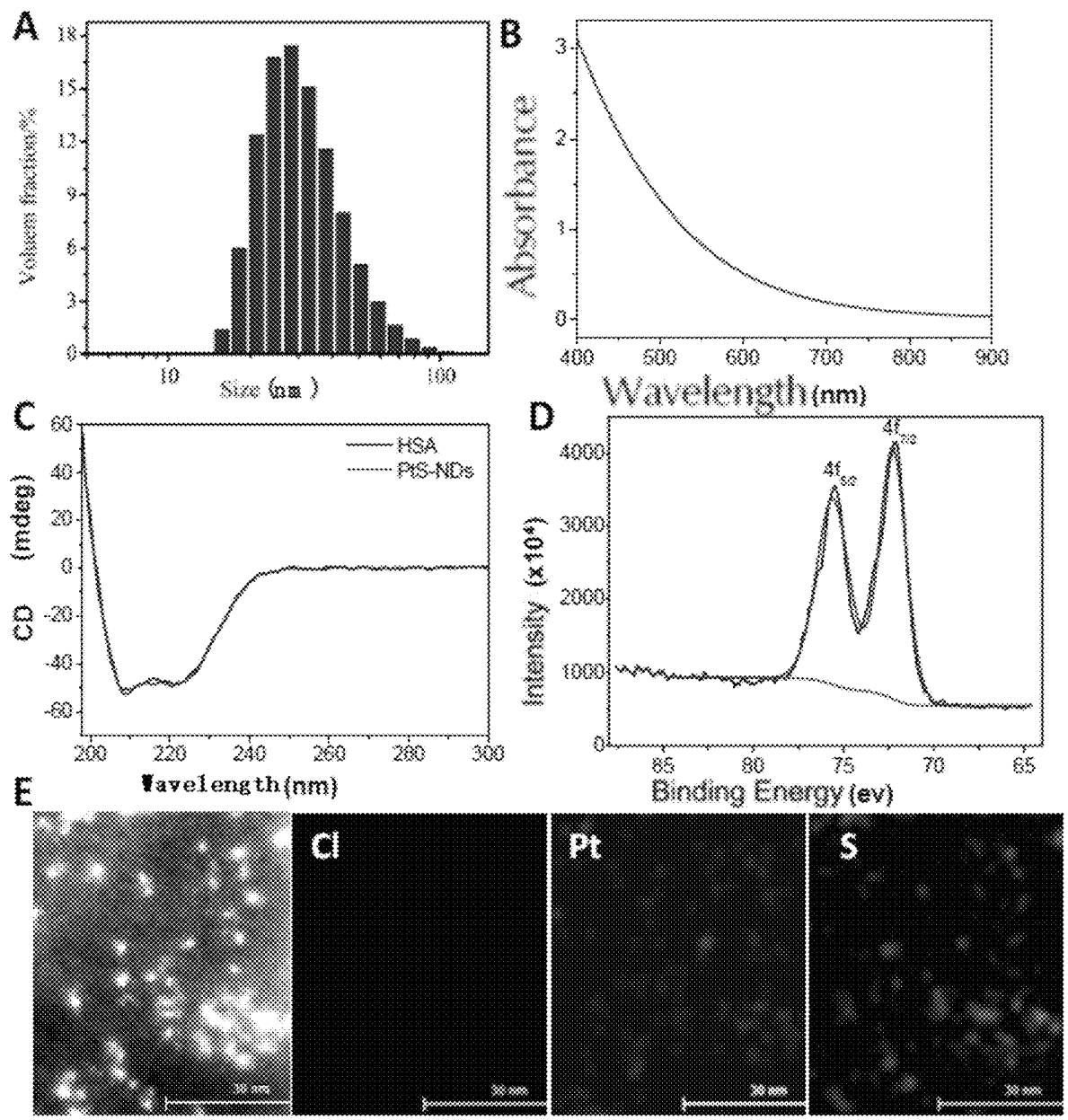
FIG. 2 is the further characterization map of the nanoparticles.

4. The further characterization of PtS-NDs nanoparticle, the results are shown in FIG. 2:

(1) Determination of hydrated particle size of nanoparticles PtS-NDs: The hydrated particle size of the prepared nanoparticles was measured by Dynamic Light Scattering (DLS) to be 40.2±0.5 nm, as shown in FIG. 2A;

(2) The UV-visible spectrum of nanoparticle PtS-NDs is attenuated, and there is still a small absorption at 785 nm, as shown in FIG. 2B;

(3) The circular two-chromatogram of nanoparticle PtS-NDs is shown in FIG. 2C. The results showed that there was no significant difference between the control curve of the nanoparticle and the HSA protein solution, which proved that the secondary structure of the protein was not destroyed during the preparation of the nanoparticle;

(4) The X-ray energy spectrum of the nanoparticles is shown in FIG. 2D. The results show that the valence of platinum in the nanoparticles is mainly positive divalent;

(5) The field emission transmission electron microscope (Tecnai G 2F20 S-TWIN, FEI) surface scan analysis of the nanoparticles is shown in FIG. 2E. The results show that the nanoparticles contain Pt and S elements.

Therefore, through the above transmission electron microscopy, X-ray photoelectron spectroscopy, circular dichroism and other methods, it was proved that the nanoparticles obtained by the present invention are: ultra-small platinum sulfide albumin nanoparticles with a surface hydration layer (the size is 4.5±0.4 nm).

5. Study on the in vitro heating effect of nanoparticles: PtS-NDs solutions were prepared into aqueous solutions with concentrations of 0.5, 0.75, 1.0, 1.5, and 2.0 mmol·$L^{-1}$, respectively, based on the platinum content. 785 nm laser was used to irradiate with 1.5 W $cm^{-2}$ power for 5 min. The temperature of the solution was recorded every 30 s after 5 minutes of irradiation. The results are shown in FIG. 3. It can be seen that the photothermal effect of the nanoparticles is concentration-dependent. The concentration increases and the heating effect increases significantly. When the concentration of the nanoparticles is 1.0 mM, the temperature increases by 17.5° C., and when the concentration of the nanoparticles is 2.0 mM, the temperature increases by 31.2° C. This indicates that the nanoparticles have good prospects for photothermal treatment.

6. Investigation on the photothermal conversion efficiency of nanoparticles: Take 500 microliters of 1.0 mM PtS-NDs solution and irradiate it with a 785 nm laser (1.5 W $cm^{-2}$) for 10 min, and then turn off the laser to allow the solution to naturally cool to room temperature. The solution temperature was recorded every 30 s. The results are shown in FIG. 4. The light-to-heat conversion efficiency calculation formula is:

$$\eta = \frac{hA(T_{max} - T_{amb}) - Q_0}{I(1 - 10^{-A\lambda})},$$

Therein, his a thermal conductivity coefficient, A is a surface area of the container, $T_{max}$ is the maximum solution temperature, $T_{amb}$ is the ambient temperature, I is the laser intensity (1.5 W $cm^{-2}$), Aλ, is the absorbance value at 785 nm.

The calculated photothermal conversion efficiency of the platinum sulfide nanoparticles is 32.0%, which is much higher than the photothermal conversion efficiency values of gold rods of photothermal materials reported in the literature, such as Au nanorods (21%), Au nanoshells (13%), CuS nanocrystals (16.3%), indicating that the nanoparticles prepared by the present invention have more ideal light-to-heat conversion efficiency.

7. Investigation on the molar extinction coefficient of nanoparticles: 2 mL of 1, 2, 3, 4, 5 mmol·$L^{-1}$ PtS-NDs aqueous solution was selected, and the ultraviolet spectrum was scanned. The absorbance values of the samples at 785 nm were plotted against corresponding molar concentrations, and the results are shown in FIG. 5. The formula for calculating the molar concentration is:

$$C = \frac{N_{total}}{NVN_A}, N = \frac{\pi}{6}\frac{\rho D^3}{M}$$

Therein, ρ• is the density, D is the particle diameter, M is the molar mass, $N_{total}$ is the molar concentration of the solution.

The molar extinction coefficient of the nanoparticles of the present invention is calculated to be 1.11×$10^9$ $M^{-1}$·$cm^{-1}$, as shown in FIG. 5, which is much higher than other photothermal materials.

8. Investigation of the stability of nanoparticles (1) Study on the effect of light time on the temperature rise and morphology of nanoparticles: take 0.5 mL of 1.0 mM PtS-NDs solution, and iridate with a 785 nm laser (1.5 W $cm^{-2}$) for 5 minutes, then turn off the laser. After the solution naturally cooled to room temperature, the solution was irradiated again for 5 min under the same conditions, and then the laser was turned off again to allow the solution to cool naturally. This process was repeated 5 times in this way, and the temperature of the sample solution was recorded every 30 s during the process. The results are shown in FIG. 6, which shows that the highest temperature reached by each heating process is maintained at a constant level. In addition, the transmission electron microscopy image shows that the average particle size was 4.1±0.6 nm, which was not significantly different from the particle size of the nanoparticles before exposure to 4.5±0.4 nm. It was confirmed that PtS-NDs had good photostability.

(2) Further investigation of the photostability of the nanoparticles: Take 2 mL of 1.0 mM PtS-NDs (4.5 nm) solution and place them in six 2 mL EP tubes of, and then these 6 samples were irradiated with a 785 nm laser (1.5 W $cm^{-2}$) for 0, 1, 2, 4, 8, 15 minutes, and the ultraviolet absorption was scanned after the irradiation was completed. The results are shown in FIG. 7, which shows that the absorption of PtS-NDs in the near-infrared region does not change significantly within 15 minutes of irradiation, further confirming that the nanoparticles have good light stability.

(3) To investigate the physical and chemical stability of the nanoparticles: first prepare a buffer solution of pH 6.2, pH 7.4, and pH 8.0. Then, different nanoparticle solutions were prepared with three different pH buffers, deionized water and serum as solvents, and UV-visible scan was measured at 785 nm at 0, 1, 2, 4, 8, 12, 24, and 48 h to determine the absorbance of PtS-NDs in different media. The results are shown in FIG. 8, showing that 48 h PtS-NDs showed good stability in different media.

The above results show that the nanoparticles of the present invention have good stability, which is a foundation for later application.

9. MTT experiments examined the cytotoxicity of nanoparticles: 4T1 mouse breast cancer cells in logarithmic growth phase were taken and seeded in a 96-well cell culture plate at a density of 5000 per well, and cultured in a 37° C. cell incubator for 24 h. Then 20 μL of different concentrations of PtS-NDs aqueous solution were added to the wells, so that the final drug concentration was 0.1, 0.5, 1, 1.5, 2 mM (quantitated by platinum). 4 Duplicate wells were set up at each concentration, and a blank control group was also set up. After 24 hours of incubation in a cell incubator, each well was washed 3 times with PBS, the remaining drug solution was washed away, fresh medium was added, and a 785 nm laser (1.5 W cm$^{-2}$) was used to irradiate each well for 5 minutes. The control group was treated with drug but not irradiation. After 24 hours of incubation, 20 μL of MTT (0.5 mg·mL$^{-1}$) solution was added to each well. After 4 hours of incubation, the solution in each well of the cell plate was carefully discard. 100 μL of dimethyl sulfoxide (DMSO) was added to each well. After 10 minutes of shaking, a microplate reader was used to detect the absorbance (OD) of each well at 490 nm. The results are shown in FIG. 9, which shows that: 1) under unirridiated conditions, the cell survival rate is greater than 80% when the concentration of PtS-NDs is 4 mM or less, indicating that it does not show obvious cytotoxicity and is relatively safe; 2) after irradiation at 785 nm, the killing effect of PtS-NDs on tumor cells was greatly enhanced, and is concentration dependend. The IC50 of the nanoparticles was calculated to be 1.13 mM.

10. In vivo distribution and antitumor effect of nanoparticles (1) A tumor model was constructed: each mouse was subcutaneously injected with 2×10$^6$ logarithmic mouse breast cancer 4T1 cells at the right back. When the tumor volume of the mouse reached 60 mm$^3$, it can be used. The formula for calculating tumor volume is V=a*b$^2$/2 (a is the tumor diameter and b is the tumor diameter).

(2) Investigation of the tissue distribution of nanoparticles: PtS-NDs (80 μmol·kg$^{-1}$) were injected into the tail vein of tumor-bearing mice, and three mice were placed in one group. Twenty-four hours after injection, the mice were sacrificed and dissected by cervical dislocation. Heart, liver, spleen, lung, kidney, and tumor were removed, weighed and recorded. They were then placed in conical flasks and added with aqua regia and perchloric acid. The sample was subjected to high-temperature nitration. Finally, the content of Pt in the sample was determined by ICP-MS. The results are shown in FIG. 10. It is shown that although the enrichment of PtS-NDs in mice, liver, kidney and tumor sites is significantly higher than other tissues and organs, but because of the low toxicity (low dark toxicity) of PtS-NDs under non-irradiation conditions, it is possible that laser can be controlled to only irradiate the tumor site, producing a photothermal effect to kill tumor cells, thereby avoiding effects on the liver and kidneys.

(3) Investigation on the antitumor effect of nanoparticles on tumor-bearing mice: To investigate the therapeutic effect of PtS-NDs with different sizes (average particle size: 4.5 nm, 3.2 nm, 2.1 nm) on tumors. Tumor-bearing mice were randomly divided into groups, with 5 mice in each group. PBS was used as a negative control, and 4.5 nm, 3.2 nm, and 2.1 nm PtS-NDs were administered as the experimental group, and the non-irradiation group and the irradiation group were set. The tail vein was injected with 200 μL of PBS or 80 μmol kg$^{-1}$ PtS-NDs aqueous solution (quantified by platinum), and 24 hours later, the tumor in the irradiation group was irradiated with a 785 nm laser (1.5 W cm$^{-2}$) for 5 min, and then the daily tumor volume was measured with a vernier caliper. The tumor growth was recorded and calculated, and the monitoring was continued for 30 days.

Thirty days later, mice were sacrificed by cervical dislocation, and tumors were removed and photographed. The results are shown in FIG. 11. Among them, FIG. 11A is shown a tumor growth curve of tumor-bearing mice in each group within 30 days, and FIG. 11B is shown a tumor picture of mice at 30 days. The results showed that: 1) the tumor growth of mice in the PBS group was similar under light and non-irradiation conditions, indicating that irradiation alone had no inhibitory effect on the tumor; 2) the nonirradiated group with injection of 2.1 nm, 3.2 nm, 4.5 nm PtS-NDs (80.0 μmol kg$^{-1}$) also did not show a significant tumor suppressing effect.

The final tumor size grew about 30 times the original, indicating that the injection of PtS-NDs alone had no tumor suppressing effect; however, 3) for 2.1 nm PtS-NDs group, laser irradiation (785 nm, 1.5 W cm$^{-2}$, 5 min) was applied 24 hours after injection, and the tumors of the mice had scabs and shed, but recurrence began on the 7th day; 4) for 3.2 nm PtS-NDs group, after irradiation, the tumors of the mice developed scabbing and shedding, but two recurrences occurred on the 16th day, and the other three tumors completely eliminated without recurrence; 5) for the 4.5 nm PtS-NDs group, laser irradiation 24 h after injection, the tumors of the mice were scabbed and no recurrence was seen within 30 days, indicating that 4.5 nm PtS-NDs can completely eliminate the tumors in mice. Therefore, 4.5 nm PtS-NDs was determined for subsequent experiments.

11. Investigation of the effect of nano-modal multi-modal imaging:

(1) Investigation on the effect of near-infrared fluorescence imaging of nanoparticles: 200 μL of Cy7.5 labeled PtS-NDs solution (4.5 nm) at a concentration of 80 μmol·kg$^{-1}$ was injected into the tail vein of tumor-bearing mice, with 3 mice in each group, at 0, 2, 4, 8, 12, 24, 48, and 72 h. Whole-body fluorescence scanning of mice was performed using a small animal in vivo imaging system. The fluorescence of food and tissues in the body was processed and subtracted using software pop separation. The results are shown in FIG. 12. FIG. 12A shows: Cy7.5-labeled PtS-NDs fluorescence signal in vivo: 1) appeared in the liver at first, and then rapidly decayed; 2) fluorescence signal appeared at the tumor site 4 h after injection, and 8 h, 12 h, 24 h brightness gradually increased, and continued to 48 h, 72 h. The fluorescence intensity of the tumor site was most obvious at 24 h, and it was not completely eliminated within 3 days. FIG. 12B shows the fluorescence intensity value of the tumor site automatically circled by the ROI. The values show the same result. The fluorescence signal of the tumor site gradually increased in the first 24 h, reached a peak at 24 h, began to weaken at 48 h, and remained at 72 h. Fluorescent signal. This indicates that Cy7.5-labeled PtS-NDs can effectively target tumors and stay in tumor sites for a long time. In addition, it can be seen from the fluorescence images of mice that near-infrared fluorescence imaging has high sensitivity, can clearly mark tumor areas, display boundaries, and can effectively guide PTT.

(2) Photoacoustic imaging of nanoparticles: 200 μL PtS-NDs (80 μmol·kg$^{-1}$) was injected into the tail vein of tumor-bearing mice and excited by 785 nm laser at 0, 2, 4, 8, 12, 24 At 48, 72 h. The photoacoustic signal at the tumor site was collected and the fluorescence intensity value was calculated by software. The results are shown in FIG. 13. PtS-NDs can produce obvious photoacoustic signals at the tumor site under laser irradiation, and the signals gradually increase from 4 h to 24 h, and the photoacoustic signals cover the entire tumor, and the dispersion is more uniform, indicating that PtS-NDs After entering the tumor, it can penetrate into the entire tumor, providing information for the localization monitoring of deep tumors.

(3) Investigation of CT imaging effects of nanoparticles: tumor-bearing mice were injected intratumorally with a dose of 150.0 µmol·kg$^{-1}$ of PtS-NDs, and small animals were used at 0, 5, 10, 30, 60, and 120 min after injection. The CT machine collected CT signals from the whole body of the mouse and three-dimensional reconstruction was performed. The results are shown in FIG. 14A, and the signal values were plotted, as shown in FIG. 14B. It can be seen that: 1) At 0 min, the brightness of the tumor site is not significantly different from the nearby muscle tissue, making it difficult to distinguish the tumor boundary; 2) After injection of PtS-NDs, the tumor site became significantly brighter, which is significantly different from the surrounding normal tissues, and the tumor boundary was obvious. Compared with the clinically used contrast agent iohexol, tumors injected with PtS-NDs are brighter and more pronounced. This shows that PtS-NDs can significantly enhance the CT value of tumor sites and is a potential CT contrast agent.

(4) Thermal imaging investigation of nanoparticles: 200 µL of different sizes of PtS-NDs (80 µmol·kg$^{-1}$) were injected into tumor-bearing mice's tail vein. After 24 h of injection, 200 µL of mice were injected intraperitoneally at a concentration of 35 mg·mL$^{-1}$. Chloraldehyde hydrate was used for anesthesia, and then the tumor site of the mouse was irradiated with a 785 nm laser at a power of 1.5 W cm$^{-2}$ for 5 min. The whole body temperature of the mouse was monitored using a near-infrared thermal imager. The result was shown in FIG. 15.

FIG. 15A shows a thermal image of a mouse. Compared to a cryptic control group injected with PBS, the brightness of the tumor site of the mouse is greater after PtS-NDs injection. FIG. 15B shows that as the size of the nanoparticles increases, the temperature of the tumor site increases. Under the same irradiation conditions, the temperature increase of the tumor site was limited by the injection of PBS; for 300 seconds (5 min), PtS-NDs at 2.1 nm further increased the temperature of the tumor site by 9° C.; and PtS— at 3.2 nm and 4.5 nm NDs can further increase the temperature of the tumor site by 13.0° C. and 20.0° C., respectively. The PtS-NDs of 4.5 nm in this paper make the temperature of the tumor site reach above 50° C. (can make the tumor heat ablate), which has very good photothermal treatment effect.

Therefore, the ultra-small platinum sulfide protein nanoparticles with near-infrared photothermal effect and multi-modal imaging function of the present invention have good tumor treatment effect, and can be used for multi-infrared fluorescence imaging, photoacoustic imaging, CT imaging and thermal imaging. Modal complementary tumor diagnosis, ultra-small particle size can be excreted by the kidney and is relatively safe. It has the potential to achieve clinically accurate integration of tumor diagnosis and treatment. At the same time, it should be pointed out that, based on the technical principle of the present invention, several improvements and modifications can be made, and these improvements and modifications should also be regarded as the protection scope of the present invention.

Example 2

When the platinum sulfide protein nanoparticles were prepared in Example 1, the human serum albumin concentration was adjusted to 4, 8 mg/mL (in Example 1, the protein concentration was 2 mg/mL), and other steps were the same as in Example 1. Two kinds of nanoparticles with a size of 3.2±0.2 nm and 4.5±0.4 nm can be prepared, and PtS-NDs with a concentration of 1.0 mM were irradiated at (785 nm, 1.5 W cm$^{-2}$) for 5 minutes at 16° C. and 18.5° C., the light-to-heat conversion efficiency was 28.7% and 31.2%, respectively.

Example 3

The reaction time during the preparation of the platinum sulfide protein nanoparticles in Example 1 was adjusted to 1 h (in Example 1, the reaction time was 4 h), the absorption in the near infrared region was maximized and maintained stable, and a size of about 4.5 nm could be prepared. PtS-NDs at a concentration of 1.0 mM can increase the solution temperature by 19.5° C. for 5 min of irradiation at (785 nm, 1.5 W cm$^{-2}$), and the photothermal conversion efficiency is 31.8%.

Example 4

During the preparation of platinum sulfide protein nanoparticles in Example 1, the molar ratios of platinum element to sulfur element were adjusted to 1:1 and 1:8 (in the first embodiment, the molar ratio of Pt:S was 1:4), and others conditions are the same as in Example 1. PtS nanoparticle with good stability can be prepared, the size was between 3.5 and 4.5 nm, 1.0 mM PtS-NDs was irradiated (785 nm, W cm$^{-2}$) for 5 min. After the irradiation, the temperature of the solution were increased to 15.5° C. and 17.3° C., respectively, and the light-to-heat conversion efficiency was 28.8% and 30.3%, respectively.

FIG. 16 illustrates that the present invention uses a protein as a nanoreactor and a Pt$^{2+}$ and S$^{2-}$ precipitation reaction to prepare platinum sulfide protein nanoparticles, and uses the permeability and retention effect (EPR effect) of solid tumor cells to enter cells. Under the irradiation of near-infrared light, the nanoparticles have good photothermal effects, and can be used for thermal imaging, photoacoustic imaging, and near-infrared fluorescence imaging. At the same time, because of the large atomic number of platinum, it has X-ray attenuation properties, which can be used for CT imaging. With compatible protein materials, nanoparticles are synthesized by a simple method for multimodal imaging guided tumor photothermal treatment. It can be known from the above that the present invention designs and prepares an ultra-small platinum sulfide protein nanoparticle with near-infrared photothermal effect and multi-modal imaging function. The visual diagnosis method using four modern diagnostic equipment greatly improves the accuracy and precision of tumor diagnosis, and can effectively play the role of photothermal treatment of tumors under external laser irradiation. At the same time, because of its ultra-small particle size, it can be excreted through the kidney and has good biological safety. There are safety issues that inorganic drugs cannot eliminate from the body. Therefore, the present invention has the advantages of accurate diagnosis of tumors, good curative effect, safety, and simple preparation of nanoparticles, and has achieved very prominent effects, and has the potential for further development and clinical application.

The invention claimed is:

1. A method of preparing a platinum sulfide protein nanoparticle with near-infrared photothermal effect and multi-modal imaging function, consisting of the following steps:
   mixing a platinum dichloride solution with a protein solution,
   adding sodium sulphide solution,
   reacting to form a mixture, and
   dialyzing and ultrafiltrating the mixture to obtain the platinum sulfide protein nanoparticle with near-infrared photothermal effect and multi-modal imaging function,
   wherein a concentration of the platinum dichloride solution is 2 to 8 mmol/L; a concentration of the protein solution is 1 to 9 mg/mL; a concentration of the sodium sulphide solution is 1-50 mmol/L; a volume ratio of the platinum dichloride solution, the protein solution, and the sodium sulfide solution is 1:0.2:0.05;
   wherein a reaction temperature is 0 to 55° C., a reaction time is 0 to 5 h;
   wherein a cut-off molecular weight for dialyzing is 3500 kD, dialyzing dialysis time is 1 to 24 h, a receiving medium for dialyzing is deionized water, and the receiving medium is changed 6 to 8 times; and
   wherein a cut-off molecular weight for ultrafiltrating is 100 kD, a rotation speed of ultrafiltrating is 1500 to 4000 r/min, and a number of ultrafiltrating is at least 20 times.

2. A method of preparing a reagent with near-infrared photothermal effect and multi-modal imaging function, consisting of the following steps:
   mixing a platinum dichloride solution with a protein solution,
   adding a sodium sulphide solution,
   reacting to form a mixture; and
   dialyzing and ultrafiltrating the mixture to obtain a platinum sulfide protein nanoparticle with near-infrared photothermal effect and multi-modal imaging function, and
   dispersing the platinum sulfide protein nanoparticle with deionized water to obtain the reagent with near-infrared photothermal effect and multi-modal imaging function,
   wherein a concentration of the platinum dichloride solution is 2 to 8 mmol/L; a concentration of the protein solution is 1 to 9 mg/mL; a concentration of the sodium sulphide solution is 1-50 mmol/L; a volume ratio of the platinum dichloride solution, the protein solution, and the sodium sulfide solution is 1:0.2:0.05;
   wherein a reaction temperature is 0 to 55° C., a reaction time is 0 to 5 h;
   wherein a cut-off molecular weight for dialyzing is 3500 kD, dialyzing dialysis time is 1 to 24 h, a receiving medium for dialyzing is deionized water, and the receiving medium is changed 6 to 8 times; and
   wherein a cut-off molecular weight for ultrafiltrating is 100 kD, a rotation speed of ultrafiltrating is 1500 to 4000 r/min, and a number of ultrafiltrating is at least 20 times.

3. The method according to claim 1, wherein a diameter of the platinum sulfide protein nanoparticle with near-infrared photothermal effect and multi-modal imaging function is 1 to 5 nm.

4. The method according to claim 3, wherein the platinum sulfide protein nanoparticle with near-infrared photothermal effect and multi-modal imaging function consists of a platinum sulfide protein nanoparticle scaffold and a the platinum sulfide core.

* * * * *